United States Patent [19]

Merianos et al.

[11] 3,968,246

[45] July 6, 1976

[54] DISINFECTING WITH N-TRIMETHYLBENZYL ETHYLENEDIAMINE

[75] Inventors: John J. Merianos, Jersey City; Phillip Adams, Murray Hill, both of N.J.

[73] Assignee: Millmaster Onyx Corporation, New York, N.Y.

[22] Filed: July 10, 1975

[21] Appl. No.: 594,581

Related U.S. Application Data

[60] Continuation-in-part of Ser. No. 549,170, Feb. 12, 1975, which is a division of Ser. No. 360,448, May 15, 1974, Pat. No. 3,886,284, which is a continuation-in-part of Ser. No. 291,824, Sept. 25, 1972, Pat. No. 3,837,197, which is a continuation-in-part of Ser. No. 130,783, April 2, 1971, Pat. No. 3,821,407.

[52] U.S. Cl. .................................. 424/330; 71/67; 162/161; 252/106; 252/107

[51] Int. Cl.$^2$ .................................... A61K 31/135
[58] Field of Search ............ 424/330; 252/106, 107

[56] References Cited
UNITED STATES PATENTS

| | | | |
|---|---|---|---|
| 3,645,715 | 2/1972 | Daum et al. ............................ | 71/67 |
| 3,689,504 | 9/1972 | Horrom ............................ | 424/330 X |
| 3,697,589 | 10/1972 | Menasse et al. ................ | 424/330 X |

*Primary Examiner*—James O. Thomas
*Assistant Examiner*—Vera C. Clarke
*Attorney, Agent, or Firm*—Arthur A. Jacobs

[57] ABSTRACT

A method of disinfecting hard surfaces by applying thereto N-trimethylbenzyl ethylenediamine, and the use of said compound in admixture with anionic, cationic or non-ionic surfactants to provide a disinfectant and cleansing composition.

3 Claims, No Drawings

DISINFECTING WITH N-TRIMETHYLBENZYL ETHYLENEDIAMINE

This is a continuation-in-part of co-pending application Ser. No. 549,170, filed Feb. 12, 1975, which is, in turn, a division of application Ser. No. 360,448, filed May 15, 1974 and issued as U.S. Pat. No. 3,886,284 on May 27, 1975, the latter being a continuation-in-part of application Ser. No. 291,824, filed Sept. 25, 1972, now U.S. Pat. No. 3,837,197, which was a continuation-in-part of application Ser. No. 130,783, filed Apr. 2, 1971 and issued as U.S. Pat. No. 3,821,407 on June 28, 1974.

This invention relates to a new and novel disinfectant which is effective in the disinfection of hard surfaces such as hospital floors, walls, manufacturing equipment, etc., and is, at the same time, compatible with anionic, cationic and non-ionic surfactants and detergents, so that it can be used together with them in a single formulation.

In the aforesaid application Ser. No. 360,448, it was shown that N-trimethylbenzyl ethylenediamine was a very effective and potent bactericide, fungicide and algicide, as well as being a good preservative, sanitizer, and disinfectant.

It has now been discovered that N-trimethylbenzyl ethylenediamine is a potent hard surface disinfectant and is compatible with anionic, cationic and non-ionic surfactants and detergents. It is, therefore, possible to include both N-trimethylbenzyl ethylenediamine and any kind of detergent in one formulation which can be used both to disinfect and cleanse hard surfaces simultaneously.

In addition, it is possible to emulsify or disperse N-trimethylbenzyl ethylenediamine in aqueous solution with either anionic, cationic or non-ionic surfactants. This gives a formulation containing commercially available disinfectants a considerable amount of flexibility, so that other additives may be incorporated without being limited by the nature of the surfactant.

The best known commercially important organic disinfectants may be divided into three main groups, for convenience, namely: quaternary ammonium salts, phenolic derivatives, and pine oil.

The quaternary ammonium salts, being cationic in nature, are incompatible with anionic surfactants and detergents.

Phenolic compounds are known to lose their ability to disinfect when they are in the presence of non-ionic surfactants or detergents, and often lose all of their disinfection activity within a matter of hours.

Pine oil, although itself compatible with all three classes of surfactants and detergents, has such a low order of effectiveness, that it must be fortified with auxiliary disinfecting agents in order to make the formulation effective at reasonable concentrations in aqueous solution. Since the auxiliary disinfecting agents are generally quaternary ammonium salts and phenolic compounds, these fortifying materials limit the choice of emulsifier or detergent which may be included in the formulation.

N-trimethylbenzyl ethylenediamine, on the other hand, is neither a quaternary ammonium salt, nor a phenol, and it is compatible with all classes of surfactants.

EXAMPLE 1

The preparation of 2,4,5 trimethylbenzyl chloride

Pseudocumene was chloromethylated by the procedure described by R. D. Lake and B. B. Corson, in the Journal of Organic Chemistry, Volume 24, pp. 1823-4. After purification by distillation, 2,4,5-trimethylbenzyl chloride was obtained in a yield that was about 80% of theoretical.

EXAMPLE 2

The preparation of N-2,4,5-trimethylbenzyl ethylenediamine 150 grams of ethylenediamine (about 2.5 moles) was placed in a round-bottom flask fitted with a stirrer, reflux condenser and dropping funnel. The dropping funnel was charged with 84 grams of purified trimethylbenzyl chloride from Example 1 (about 0.5 moles), and the chloride was added slowly to the amine. The temperature was maintained at reflux with constant stirring.

The addition took about 30 minutes. The adduct was then cooled. Analysis for ionic chloride showed that the reaction was about 100% complete.

Thereafter, about 100 ml. of 30% aqueous caustic was added, with stirring, to liberate the product from its hydrochloride salt, and the free amine was extracted with about 500 ml. of chloroform in a separating funnel.

After stripping the chloroform, the pure amine product was obtained in about 95% of theoretical yield by distillation at 122°-125°C at 0.1 mm.

The undistilled amine was found to be suitable for commercial purposes, after stripping off the chloroform.

The hydrochloride of the pure amine melted at 172°-174°C.

N-trimethylbenzyl ethylenediamine, together with inactive surfactants, was tested for microbiocidal activity against P. aeruginosa using the "Use Dilution Test" as described in "Official Methods Of Analysis Of The Association Of Official Analytical Chemists", 11th edition, 1970, page 61, published by the Association Of Official Analytical Chemists, Washington, D.C.

The passing criteria was at least 59 negative subcultures in 60 replicates at the indicated concentration in ppm. of the tested compound. After establishing a minimum lower concentration, some samples were tested at a higher concentration using 30 replicates.

The following tables are based on the number of negative subcultures over the number of replicate steel cylinders inoculated with P. aeruginosa and exposed to various dilutions of the experimental compound for 10 minutes prior to subculture in Letheen broth. In these tables N,2,4,5-trimethylbenzyl ethylenediamine is "Compound B", "Permakleer 100" is the tetrasodium salt of ethylenediamine tetracetic acid, 40% aqueous solution, "N 656" is nonyl phenol polyethyleneoxide (11 moles), and "Maprofix WAC" (manufactured by the Onyx Chemical Co., Jersey City, N.J.) is sodium lauryl sulfate, 30% aqueous solution.

Table 1

| Formulation | I (Parts by Wt.) | II (Parts by Wt.) |
|---|---|---|
| Compound B | 4.5 | 4.5 |
| "N 656" | 4.5 | |
| "Maprofix WAC" | | 10.0 |
| Water | 91.0 | 85.5 |

Table 1-continued

| Formulation | I (Parts by Wt.) | II (Parts by Wt.) |
|---|---|---|
| | 100.0 | 100.0 |

Table 2

| | Formulation I | Formulation II |
|---|---|---|
| 3 oz/gallon(equivalent to 1050 ppm of compound B) | 54/60 52/60 58/60 | 48/60 60/60 48/60 |
| 4 oz/gallon(equivalent to 1400 ppm of compound B) | 60/60 60/60 60/60<br>30/30 30/30 30/30 | 60/60 60/60 60/60<br>30/30 30/30 30/30 |
| 5 oz/gallon(equivalent to 1750 ppm of compound B) | 60/60 60/60 60/60<br>30/30 30/30 30/30 | 60/60 60/60 60/60<br>30/30 30/30 30/30 |

The results of the "Use Dilution Test" show that the compound of this invention is an effective disinfectant at concentrations of about 1400 ppm and above used together with either non-ionic or anionic surfactants. There is no maximum concentration since all concentrations above about 1400 ppm are obviously effective.

These minimum effective concentrations substantially exceed those of the very best quaternary salts used alone, for disinfection. But, unlike the quaternary ammonium salts, the compound of the present invention can also be used effectively with anionic surfactants or detergents.

The minimum effective concentration of phenol disinfectants is of the same order of magnitude as the quaternary ammonium salts, but, unlike the compound of the present invention, phenol disinfectants cannot be used together with non-ionic surfactants and detergents.

It is to be understood that the surfactants used in these tests are merely exemplifications of such surfactants generally, any of which can be used for the same purpose. In this respect, the following types of surfactants are illustrative of those which may be utilized:

Anionic surfactants: alkyl sulfate salts, alkyl polyethyleneoxy sulfate salts, alkyl phenol polyethyleneoxy sulfate salts, alkylbenzene sulfonate salts, olefin sulfonate salts, -acylamido propionate salts, sarcosinates, taurates, and fatty acid salts.

Non-ionic surfactants: alkyl polyethyleneoxy ethers, alkyl phenol polyethyleneoxy ethers, polyethyleneoxy amines, polyethyleneoxy fatty acids, alkyl dimethyl amino oxides, and the "Pluronics" (BASF - Wyandotte, Mich.)

Cationic surfactants: alkyltrimethyl ammonium halides, dialkyldimethyl ammonium halides, alkylbenzyl dimethyl ammonium halides, and imidazolinium salts, pyridinium salts, and quinolinium salts.

Specific surfactants utilizable in this invention are, inter alia, those disclosed, for example in, "Surface Active Agents and Detergents", Schwartz, Perry and Berch, Interscience Publishers, Inc., New York, 1958, Vol. I, 1949–1963, Vol. II, 1958.

The invention claimed is:

1. A method of disinfecting a surface which comprises applying to said surface an effective amount sufficient to disinfect said surface of N-trimethylbenzyl ethylenediamine.

2. The method of claim 1 wherein the N-trimethylbenzyl ethylenediamine is in admixture with water and an effective amount sufficient to cleanse said surface of a surfactant selected from the group consisting of anionic, cationic and non-ionic surfactants.

3. The method of claim 2 wherein the concentration of the N-trimethylbenzyl ethylenediamine in the mixture is at least 1400 ppm.

* * * * *